United States Patent [19]

Guilard et al.

[11] Patent Number: 5,434,262

[45] Date of Patent: Jul. 18, 1995

[54] PROCESS FOR THE SYNTHESIS OF CYCLIC POLYNITROGENATED COMPOUNDS

[75] Inventors: Roger Guilard, Fontaine les Dijon; Isabelle Meunier, Tournus; Christophe Jean, Chenove; Brigitte Boisselier-Cocolios, Limours, all of France

[73] Assignee: L'Air Liquide, Societe Anonyme Pour L'Etude et L'Exploitation des Procedes Georges Claude, Paris, France

[21] Appl. No.: 945,575

[22] Filed: Sep. 16, 1992

Related U.S. Application Data

[63] Continuation of Ser. No. 610,919, Nov. 9, 1990, abandoned.

[30] Foreign Application Priority Data

Nov. 9, 1989 [FR] France .................. 89 14719

[51] Int. Cl.$^6$ ............................... C07D 487/22
[52] U.S. Cl. ......................... 540/474; 540/465; 540/468; 540/471; 540/473
[58] Field of Search ............. 540/465, 468, 471, 473, 540/474

[56] References Cited

U.S. PATENT DOCUMENTS

| | | | |
|---|---|---|---|
| 4,001,212 | 1/1977 | Richman ............... | 260/239 |
| 4,174,428 | 11/1989 | Tabushi et al. ............ | 540/465 |

FOREIGN PATENT DOCUMENTS

| | | | |
|---|---|---|---|
| 0287436 | 10/1988 | European Pat. Off. ........... | 540/474 |
| 8705030 | 8/1987 | WIPO ................ | 540/474 |
| 89/01476 | 2/1989 | WIPO . | |

OTHER PUBLICATIONS

Lacon, et al. Chem. Abs. vol. 101, 1984 Abs. 72912a.
Lacon, et al. Chem. Abs. vol. 101, 1984 Abs. 72901w.
Kadish, et al. Chem. Abs. vol. 101, 1984 Abs. 62438m.
Cocolios, et al. Chem. Abs. vol. 101, 1984 Abs. 54772q.
Chang, et al. Chem. Abs. vol. 100, 1984 Abs. 199669m.
Lagrange, et al. Chem. Abs. vol. 100, 1984 Abs. 156765.
Kim, et al. Chem. Abs. vol. 98, 1982 Abs. 4489n.
Cocolios, et al. Chem. Abs. vol. 99, 1983 Abs. 175446w.
Cocolios, et al. Chem. Abs. vol. 97, 1982 Abs. 55971q.
Cocolios, et al. Chem. Abs. vol. 97, 1982 Abs. 6490j.
Lecomte, et al. Chem. Abs. vol. 94, 1988 Abs. 75017k.
Cocolios, et al. Chem. Abs. vol. 93, 1980 Abs. 249221u.
Rapoll, et al. Chem. Abs. vol. 93, 1980 Abs. 109874j.
Cocolios, et al. Chem. Abs. vol. 92, 1979 Abs. 42022p.
Guilard, et al. Chem. Abs. vol. 91, 1979 Abs. 20471n.
Guilard, et al. Chem. Abs. vol. 87, 1977 Abs. 23364q.
Campo, et al. Chem. Abs. 116, 1991, Abs. 58965y.

(List continued on next page.)

Primary Examiner—Mukund J. Shah
Assistant Examiner—P. K. Sripada
Attorney, Agent, or Firm—Browdy and Neimark

[57] ABSTRACT

A method for the synthesis of cyclic polyamines preceeds by reaction of a diamine with the acrylonitrile wherein the reduction steps are carried out with Raney alloy instead of using hydrogen under pressure in the presence of Raney nickel. Compounds so prepared have the formula:

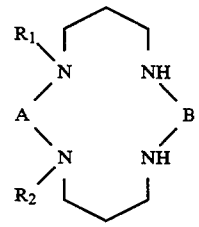

wherein A and B are: an alkyl chain —(CH$_2$)$_x$— in which x is an integer of 2 to 4, substituted or not by an alkyl group of 1 to 5 carbon atoms, which may be substituted or not by an aromatic ring, heterocyclic ring, amine ketone, carboxylic acid, amide, cyano, alkyl, alkoxy, hydroxy, nitro or halogen and R$_1$ and R$_2$ are the same moieties as those substituting the alkyl claim above.

8 Claims, No Drawings

Page 2

OTHER PUBLICATIONS

Amatore, et al. Chem. Abs. vol. 116, 1991 Abs. 23916f.
Campo, et al. Chem. Abs. vol. 112, 1989 Abs. 55234r.
Guilard, et al. Chem. Abs. vol. 110, 1988 Abs. 30351x.
Ledon, et al. Chem. Abs. vol. 109, 1988 Abs. 213215e.
Ledon, et al. Chem. Abs. vol. 108, 1987 Abs. 192278q.
Tabard, et al. Chem. Abs. vol. 108, 1987 Abs. 38080n.
Kadish, et al. Chem. Abs. vol. 103, 1985 Abs. 149408s.
Kadish, et al. Chem. Abs. vol. 103, 1985, Abs. 61313w.
Kadish, et al. Chem. Abs. vol. 104, 1985 Abs. 12127a.
Guilard, et al. Chem. Abs. vol. 103, 1985 Abs. 53607e.
Kadish, et al. Chem. Abs. vol. 103, 1985 Abs. 29099v.
Cocolios, et al. Chem. Abs. vol. 103, 1985 Abs. 29089s.
Cocolios, et al. Chem. Abs. vol. 103, 1985 Abs. 15928.
Oumous, et al. Chem. Abs. vol. 102, 1984 Abs. 45405.
Cocolios, et al. Chem. Abs. vol. 101, 1984 Abs. 139573.
Bull, et al. Inorganic Chemistry, 1987 26 3040–3043.
Chemical Abstract, vol. 85, No. 8, 23 Aug. 1976, p. 662, resume No. 56001y, Colombus, Ohio, U.S.; E. K. Barefield et al. "[Preparation of] (1,4,8,11-tetraazacyclotetradecane) nicke 1(II) perchlorate . . . ", & Inorg Synth. 1976, 16, 220–5.
Chemical Abstract, vol. 83, No. 19, Nov. 10, 1975, p. 460, resume No. 163035t, Colombus, Ohio, U.S.; W. Wehner et al. "Cyclam, a macroheterocyclis ligand. Synthesis, complex formation, and ligand. Synthesis of 1,4,8,11-tetraazacyclotetradecane (cyclam) bia the nickel(II) complex".
The Journal of the American Chemical Society, vol. 67, Jan.–Jun. 1945, pp. 92–94, Mack Printing Co., Baston Pa.; S. R. Buc et al. "An improved synthesis of beta-alanine".
Inorganic Chemistry, vol. 11, No. 9, Sep. 1972, pp. 2273–2274, American Chemical Soc.; E. K. Barefield: "A new synthesis of 1,4,8,11-tetraazacyclotetradecane (cyclam) via the nickel (II) . . . ".

PROCESS FOR THE SYNTHESIS OF CYCLIC POLYNITROGENATED COMPOUNDS

This application is a continuation of application Ser. No. 07/610,919, filed Nov. 06, 1990 abandoned.

This invention relates to a new process for the synthesis of cyclic polynitrogenated compounds.

These compounds of general formula (I)

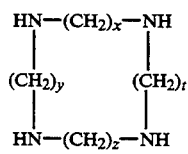

where x, y, t and z are integer numbers ranging from 2 to 4, are starting compounds for the preparation of cyclic polynitrogenated compounds, mono or poly-substituted.

Among these polynitrogenated compounds, the mono-substituted ones may be prepared by applying a substitution method to the compounds of formula (I), as described in the patent application EP N° 0287436.

However, the starting product used for the preparation of these substituted compounds, that is the macrocycle of formula (I), is prepared nowadays with very low yield at a high cost.

As an illustration, the synthesis method of the cyclam of formula (I) in which $x=z=3$ and $y=t=2$, which is so far considered as the most performant, has been proposed by BAREFIELD E. K., Inorg. Chem. (1972), 11, 2273 with the following steps:

-Step 1:

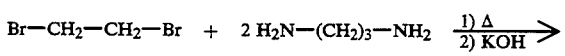

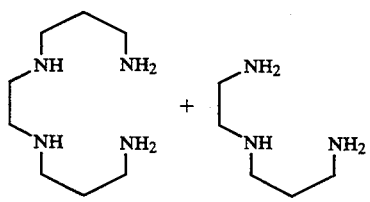

The disubstitution is not complete and the reaction leads to a mixture of two products. The synthesized tetraamine is separated from the triamine by-product also formed during this reaction, by distillation with a yield of 39%.

-Step 2:

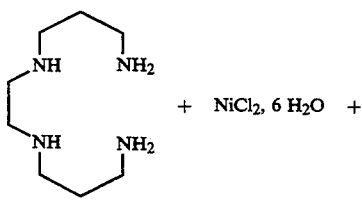

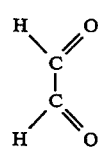

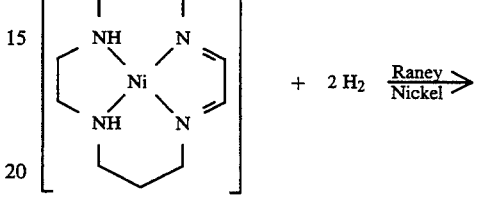

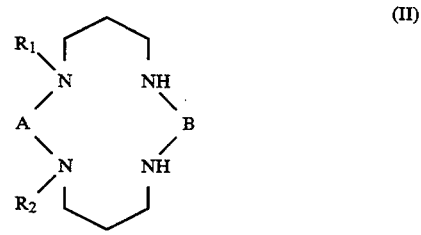

The yield of this step is of 20% in cyclam.

The yield limiting reaction is the reduction which is performed under hydrogen pressure in the presence of Raney nickel with very slow kinetics (10% conversion after two days). The global yield of these two steps for the preparation of the cyclam starting from the 1,2-dibromoethane is of 7.8%.

This invention also relates to a method for the synthesis of the macrocycle of formula (I), substituted or not by one or several substituants, this method leading to an improvement of the preparation yield compared to the yields of the known synthesis methods nowadays.

This invention relates more specifically to a method of synthesis of cyclic polynitrogenated compounds of the following general formula (II):

$$\text{(II)}$$

in which,
 the substituant A represents:
  an alkyl chain —$(CH_2)_x$— in which x represents an integer number of 2 to 4, substituted or not by one or several groups P or by one or several groups $P_1$, $P_1$ being an alkyl group of 1 to 5 carbon atoms, substituted or not by one or several groups P, where P represents:
  a group —COR in which R represents a hydroxyl (—OH), a primary amine or an amine substituted by one or two alkyl groups of 1 to 4 carbon atoms, a —OR' function in which R' represents either an alkyl group of 1 to 4 carbon atoms or an aromatic cycle of 6 to 14 carbon atoms;

- an aromatic cycle of 6 to 14 carbon atoms eventually substituted in its ortho and/or meta and/or para positions by a halogen atom, an alkyl group of 1 to 4 carbon atoms, an alkoxy group of 1 to 4 carbon atoms, a hydroxy, an aryl group, an aromatic heterocycle, a nitro group, a —$(CH_2)_u$—COR group in which R has the same meaning as above and u is an integer number ranging from 0 to 4, or a primary amine or an amine substituted by one or two alkyl groups of 1 to 4 carbon atoms.
- an aromatic heterocycle, especially a heterocycle containing a nitrogen atom, of 4 to 12 carbon atoms, eventually substituted in its ortho, and/or meta, and/or para positions by a halogen atom, an alkyl group of 1 to 4 carbon atoms, an alkoxy group of 1 to 4 carbon atoms, a hydroxy, an aromatic heterocycle, an aryl group, a nitro group, a —$(CH_2)_u$—COR in which R has the same meaning as above and u represents an integer number ranging from 0 to 4, or a primary amine or an amine substituted by one or two alkyl groups of 1 to 4 carbon atoms.
- a primary amine or an amine substituted by one or two alkyl groups of 1 to 4 carbon atoms.
- a —CN group
- an alkyl group of 1 to 4 carbon atoms
- an alkoxy group of 1 to 4 carbon atoms
- a hydroxy group
- a nitro group
- a halogen atom
- an aromatic cycle of 6 to 14 carbon atoms in which 2 carbon atoms respectively participate to a bond with the two nitrogen atoms located on each side of the constituent A in formula (II). This aromatic cycle may be substituted by one or several groups P and/or $P_1$, P and $P_1$ having the same meaning as described above.
- a group represented by —$(CH_2)$—E—$(CH_2)$— in which E represents an aromatic cycle of 6 to 14 carbon atoms, that can be substituted by one or several groups P and/or $P_1$, P and $P_1$ having the same meaning as above.

The constituent B represents a chain of formula —$CH_2$—$B_1$—$CH_2$— in which $B_1$ represents:

- an alkyl chain —$(CH_1)_x$— in which x represents an integer number ranging from 0 to 2, substituted or not by one or several groups P or by one or several groups $P_1$, P and $P_1$ having the same meaning as above,
- an aromatic cycle of 6 to 14 carbon atoms in which 2 carbon atoms respectively participate to a bond with the carbon atoms of the —$CH_2$— groups located on each side of the constituent $B_1$. This cycle may eventually be substituted by one or several groups P and/or $P_1$, P and $P_1$ having the meanings indicated above, $R_1$ and $R_2$, identical or different, represent a hydrogen atom or a group P or $P_1$, P and $P_1$ having the same meanings as above, this synthesis method being characterized by the following steps:

the reaction of a compound of formula $H_2N$—A—$NH_2$ in which A has the same meaning as described above, with the acrylonitrile of formula $H_2C$=CH—CN leading to the formation of the compound of formula (III)

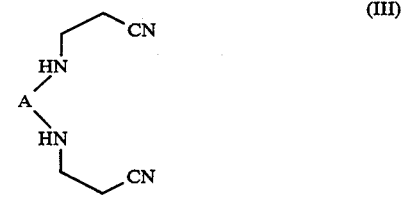

(III)

eventually, the reaction of compound (III) with one or two halides respectively of formula $R'_1X_a$ and $R'_2X_b$ in which $X_a$ and $X_b$, identical or different, represent an halogen atom (such as Cl, Br, I) and $R'_1$ and $R'_2$, identical or different, are such that at least one of them represents the group P or $P_1$, P and $P_1$ having the same meaning as above, while the other of the two groups $R'_1$ or $R'_2$, represents either a group P or $P_1$ as mentioned above or a hydrogen atom, thus leading to a compound of formula (IV)

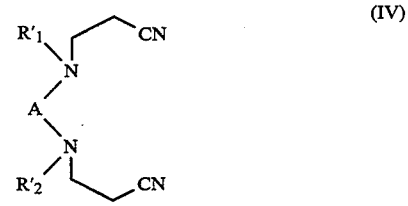

(IV)

The compounds of formula (III) and (IV) indicated above will be depicted in the following by compounds of formula (V)

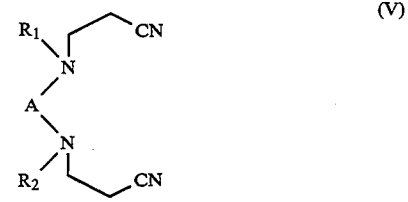

(V)

in which A, $R_1$ and $R_2$ have the same meanings as the ones indicated above, the reduction of compound of formula (V) in which the groups A, $R_1$ and $R_2$ are eventually protected by one or several appropriate protecting groups, by the Raney alloy in the presence of a base, thus leading to the formation of the compound of formula (VI)

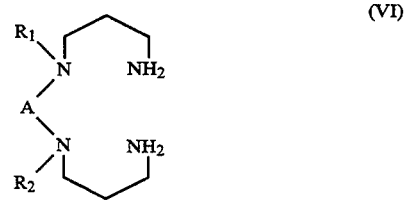

(VI)

the reaction of compound of formula (VI) with a compound of formula (VII)

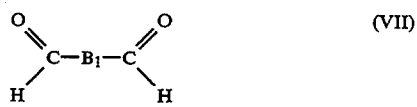

in which $B_1$ has the above mentioned meanings, in the presence of metal salt of formula MX, in which M represents a transition metal preferably chosen among the following metals Ni, Co, Cu, Fe, Mn, Cr, V, Zn, X represents an anion preferably chosen among the following $Cl^-$, $ClO_4^-$, $SO_4^=$, $NO_3^-$, $CH_3CO_2^-$, and MX is preferably a nickel salt, thus leading to the formation of a compound of formula (VIII),

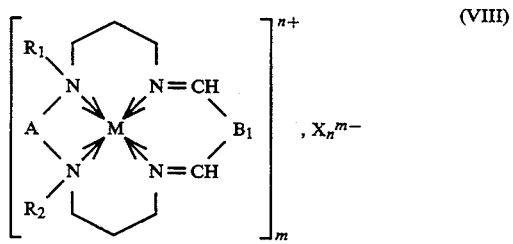

in which n represents the oxidation state of the metal and m, the charge of the anion, the reduction of the compound of formula (VIII) by the Raney alloy in the presence of a base, such as the sodium hydroxide (NaOH) or the potassium hydroxide (KOH), thus leading to the formation of compound (IX)

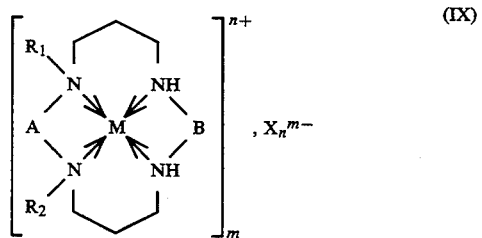

the reaction of the compound of formula (IX) with a compound Z—CN where Z represents Na or K, under conditions leading to the formation of the compound of formula (II) previously described.

Another aspect of this invention relates to a method of synthesis of cyclic polynitrogenated compounds of formula (II) in which $R_1$, $R_2$ and A have the same meaning as above and B represents an aromatic cycle of 6 to 14 carbon atoms in which two carbon atoms respectively participate to a bond with the two nitrogen atoms located on each side of the constituent B, this cycle being substituted, or not, by one or several groups P and/or $P_1$, P and $P_1$ having the same meanings as above. This synthesis is carried out according to the same steps previously described, the cyclization step excepted which is performed by reaction of a compound of formula (VI) as described above with a compound of formula O=B=O (VII his), which is the quinone form of the aromatic cycle of 6 to 14 carbon atoms, described above, in which two carbon atoms are doubly bound to an oxygen atom.

The first step of the method described in this invention leads to the formation of a dinitrile compound (compound of formula (III)) with a yield in the order of 60%. The conditions under which this reaction can proceed are described by BUC, S. R. et al, J. Am. Chem. Soc., (1945), 67, 92.

The dinitrile compound of formula (III) is then advantageously purified by distillation. The molar ratio between the diamine $H_2N$—A—$NH_2$ and the acrylonitrile in the bulk medium is preferably of the order of 1/3.

The reduction step of the dinitrile compounds (III) and (IV) (or of the compound of formula (V)) by the Raney alloy leads to the diamine of formula (VI) with a yield of 30 to 80%.

The total yield of the two steps is advantageously of the order of 50% which compares well with the 39% yield of the first step of the method described by BAREFIELD, and the cost of the reactants used in the method of this invention is by far lower than the one of the reactants used in the BAREFIELD method.

The dinitrile derivatives (III) and (IV) obtained in the first step are advantageously used without further purification in the second step of the synthesis leading to the diamine derivatives of formula (VI) with yields of 40 to 60%.

Moreover, the diamine of formula (VI) is advantageously obtained, according to this invention, without the formation of intermediate species such as the triamine, as described in the BAREFIELD method. The preparation of the macrocycle of formula (II) starting from the compound of formula (VI), follows the same experimental procedure than the one described by BAREFIELD but uses the Raney alloy (STASKUN, B., J. Chem. Soc. (C), (1986), 531) for the reduction of the imine into an amine instead of the hydrogen under pressure in the presence of Raney nickel.

The substitution of the Raney nickel by the Raney alloy presents four advantages:
all the problems related to hydrogen handling under pressure are avoided,
the kinetics of the reaction is greatly enhanced: the reduction is complete after one hour at room temperature,
the Raney alloy costs less than the Raney nickel catalyst,
the yield of the step leading to the cyclam of formula (II) where $R_1$ and $R_2$ are hydrogen atoms, A and B are a —$CH_2$—$CH_2$— chain, starting from a compound of formula (VI) is of 60%. The total yield for the preparation of the cyclam, starting from the acrylonitrile, is of 22% which is to compare with the total yield of 8% starting from the 1,2-dibromoethane according to the method of BAREFIELD.

The yield for the synthesis of the substituted compounds of formula (II), starting from a compound of formula (VI), is at least of the order of 20% and can reach 70%.

This invention also relates to the compounds of formula (II) as defined above, that are prepared according to the method of this invention.

This invention also relates to the intermediate products of formula (III) to (IX), the compounds of formula (VII) and (VIIbis) excepted, obtained in the different steps of this invention process described above, and more specifically to the compounds of formula (VI).

This invention relates more specifically to compounds of formula (II) in which:

A and B, identical or different, represent:
a chain

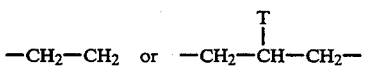

in which T represents a hydrogen atom or a group P or P₁, where P and P₁ have the same meanings as above, the group —COR excepted, and T represents particularly a group —(CH₂)$_q$—NH₂ where q is an integer number ranging from 1 to 5,
a group

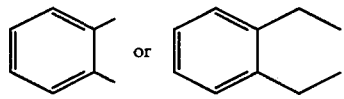

R₁ and R₂, identical or different, represent
a hydrogen atom
a group P or P₁, where P and P₁ have the same meanings as above, the —COR group excepted, and are more specifically a chain —(CH₂)$_q$—NH₂ where q has the meaning indicated above,
a group

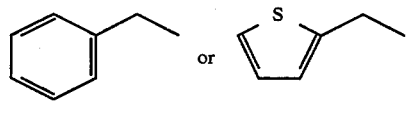

or

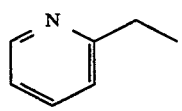

The invention also relates to compounds of formula (VI) in which A, R₁ and R₂ have the meanings indicated above for compounds of formula (II).

This invention relates also to a process for the preparation of compounds of formula (X)

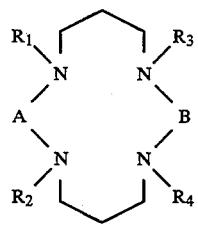

(X)

in which, A, B, R₁ and R₂ have the meaning indicated above and at least one of the groups R₃ and R₄ represents a group P or P₁, P and P₁ having the same meanings as above, while the other group R₃ or R₄ represents either a group P or P₁, as described above or a hydrogen atom, and this process proceeds according to the steps described above for the preparation of compounds of formula (II) followed by the reaction of this compound of formula (II) with one or two halides respectively of formula R₃X$_c$ and R₄X$_d$ in which X$_c$ and X$_d$, identical or different, represent a halogen atom (such as Cl, Br, I) and R₃ and R₄ have the same meanings as above.

This invention also relates to compounds of formula (X) as defined above, obtained by the above described process of this invention.

The invention is more specifically related to compounds of formula (X) in which:
A and B, identical or different, represent:
a chain

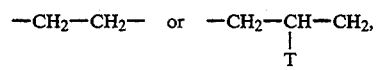

in which T represents a hydrogen or a group P or P₁, where P and P₁ have the meanings indicated above, the group —COR excepted, T being more specifically a group —(CH₂)$_q$—NH₂ where q is an integer number ranging from 1 to 5,
a group

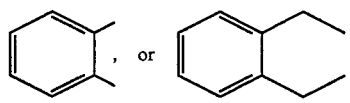

R₁ and R₄ represent a hydrogen,
R₂ and R₃, identical or different, represent
a group P or P₁, P and P₁ having the same meanings than above, the group —COR excepted, and more specifically a chain —(CH₂)$_q$—NH₂ where q has the meaning indicated above,
a group

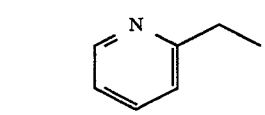 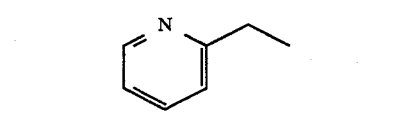

This invention also relates to the use of the compounds described above for the complexation of heavy metal cations.

Generally the compounds of this invention can be used associated to a metal, in processes for the separation and/or extraction of gases.

The compounds of this invention are especially interesting for the binding of dioxygen, particularly the binding of dioxygen from air, when they are complexed with a metal such as cobalt.

This invention is illustrated with the examples of synthesis that follow:

EXAMPLE I: synthesis of the cyclam.

Step 1.

To one mole of ethylenediamine, 3 moles of acrylonitrile are added dropwise over a period of 2 to 4 hours and preferably of 3 hours. A raise of temperature is noted from room temperature to 45° C. at maximum. The stirring is maintained during 24 to 48 hours and preferably during 32 hours and then the excess of starting products is eliminated by distillation under reduced pressure (60 mm Hg) and the remaining product is distilled under reduced pressure (0.1 mm Hg).

The expected product is isolated with a yield of 60%.
Step 2.

After dissolving 10 g of the dinitrile obtained in Step 1 in 110 to 330 mL of ethanol and preferably in 200 mL, 18 g of Raney alloy are added. The addition of 200 mL of NaOH 2N, dropwise, under vigorous stirring induces an increase of temperature. When the addition is completed, the stirring is maintained during one hour and then the bulk is left until it reaches room temperature.

After filtration of the remaining alloy over celite ®, the filtrate is evaporated. The resulting solid is dissolved in 400 mL of water and the organic product is extracted with chloroform. After drying over magnesium sulfate and evaporation of the organic solvent, 8.5 g of a yellowish oil is collected and identified as the tetraamine of general formula (VI). (yield=60%).

Step 3.

To 10 g of this tetramine dissolved in 232 mL of water, 15 g of nickel chloride hexahydrate are added. The purple solution is cooled down to 6° C. and 9.6 mL of a 40% aqueous solution of glyoxal are added dropwise. The bulk medium is kept under stirring at room temperature overnight, then 6.5 to 20 g, and preferably 12.8 g, of Raney alloy are added followed by the dropwise addition of 130 to 400 mL, and preferably 256 mL, of NaOH 2N.

After stirring for one hour at room temperature the alloy is eliminated by filtration over celite$^R$ and the filtrate is mixed with 19.2 g of sodium cyanide. The bulk medium is then heated under reflux during 3 hours.

After extraction of this solution with chloroform, drying of the organic phase over MgSO4 and evaporation of the solvent, a whitish solid is isolated.

Its purification is carried out by stirring the solid in 50 mL of acetonitrile under reflux, during 20 minutes. After filtration and washing with ether, 7.1 g of cyclam are collected. Yield 60%. $^1$H NMR (CDCl$_3$): 1.73 (g, 4H); 2.48 (s, 4H); 2.68 (s, 8H); 2.75 (t, 4H) Overall yield 21.6%.

EXAMPLE II : Synthesis of N-Benzyl 1, 4, 8, 11 tetraazacyclotetradecane.

-Step 1a.

Synthesis of 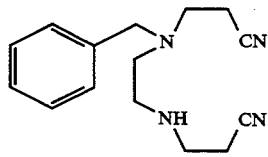

In 550 mL of absolute ethanol, cooled down at 5° C., 70 g of the dinitrile obtained in Step 1 of Example I are added, followed by the addition, dropwise, of 50 mL of benzyl bromide. The bulk medium is heated under reflux during 1 to 2 hours and preferably during 1.5 hours and then left until it reaches ambient temperature. The starting amine that did not react, protonated with HBr, and eliminated by filtration as a white solid, before evaporation of the ethanol. The orange oil obtained is then dissolved in 220 mL of water and added of 100 mL of chloroform. The pH is raised to 8 by adding NaOH and the two phases are vigorously stirred during 20 mn. After separation of the organic phase and drying over magnesium sulfate, a yellow-orange oil is isolated. By chromatography on silica column under pressure, the monobenzylated dinitrile is isolated with a yield of 60%. The solvent used for chromatography is a mixture of methylene chloride/heptane a 5/1 ratio.

-Step 2

Synthesis of 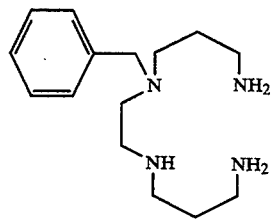

To 3.2 g of the compound obtained in the Step 1a dissolved in 30 to 100 mL, and preferably in 64mL, of ethanol, are added 3 to 9 g, and preferably 5.8 g, of Raney alloy followed by a quick dropwise addition of 30 to 100 mL, and preferably 64 mL, of 2N NaOH solution.

A vigorous stirring is maintained during 1 to 2 hours and preferably during 1.5 hours, and then the alloy is filtered off over celite ®. The solvent is evaporated, the solid is dissolved in water and the solution is extracted with chloroform. After drying of the organic phase over magnesium sulfate and evaporation of the solvent, the expected compound is isolated with a yield of 76%.

-Step 3.
Synthesis of compound of formula (II) in which A = —(CH$_2$)$_2$—, R$_1$ = CH$_2$—C$_6$H$_5$, R$_2$ = H.

Synthesis of 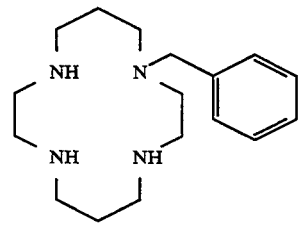

After dissolving 2 g of the tetraamine described above in 27 mL of water, 1.8 g of nickel chloride hexahydrate are added. To this dark green solution, cooled down to 6° C., 1.3 mL of a 40% solution of glyoxal in water are added. The bulk medium is then stirred at room temperature overnight, then added of 0.9 to 2.5 g, and preferably 1.7 g, of Raney alloy followed by the quick, dropwise, addition of 17 to 50 mL, and preferably 34 mL, of a 2N NaOH solution. After stirring for one hour at room temperature, the alloy is eliminated by filtration over celite.® and the filtrate is treated with 2.6 g of sodium cyanide. The bulk medium is then heated under reflux during 3 hours. After extraction of this solution with chloroform, drying of the organic phase over magnesium sulfate and evaporation, a brown oil is isolated. This oil is diluted in 40 mL of pure ethanol and protonated with concentrated sulfuric acid. The collected brown gum is then deprotonated by stirring in 50 mL of 2.5% NaOH solution. After extraction with methylene chloride, drying of the organic phase over magnesium sulfate and evaporation, the monobenzylated cyclam is isolated. Yield 50%.

The global yield is of the order of

EXAMPLE III: Synthesis of N-(3-picolyl)-1,4,8,11-tetraazacyclotetradecane.

-Step 1.

Synthesis of 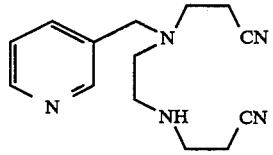

3-picolylchloride hydrochloride (0.01 mole) dissolved in 3 to 7 mL of ethanol and 1 to 3 mL of water (preferably in 5 mL of ethanol and 2 mL of water) are added dropwise to a 4° C. cooled solution of 0.032 mole of dinitrile (obtained in Step 1 of the synthesis of cyclam) in 30 to 50 mL and preferably 40 mL of ethanol. The reaction mixture is heated under reflux for 6 hours. After evaporation of the solvents under reduced pressure an oily material is isolated and redissolved in 50 mL of water and then extracted with chloroform (3 times 20 to 40 mL and preferably 30 mL of chloroform). The organic phase is dried over magnesium sulfate, filtered off and evaporated under reduced pressure. The crude oily material obtained is used in the next step without further purification.

$^1$H NMR (D$_2$O): δ2.72 (t, 2H, CH$_2$); 2.89 (t, 2H, CH$_2$); 2.90 (t, 4H, signal of the starting dinitrile) ; 3.01 (t, 2H, CH$_2$) ; 3.05 (t, 2H, CH$_2$); 3.29 (t, 2H, CH$_2$); 3.34 (t, 2H, CH$_2$); 3.37 (t, 4H, signal of the starting material) ; 3.42 (s, 4H, signal of the starting material); 4.10 (s, 2H, —CH$_2$—Py); 7.98 (t, 1H, H$_5$—Py); 8.58 (d, 1H, H$_4$—Py); 8.65 (d, 1H, H$_6$—Py); 8.79 (s, 1H, H$_2$—Py).

-Step 2.

Synthesis of 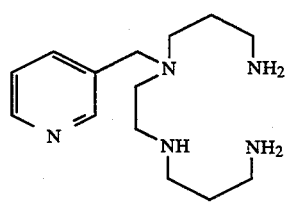

After dilution of 2 g of the oily material obtained in Step 1 in a volume of 70 to 90 mL and preferably 80 mL of ethanol, 6.3 g of Raney alloy are added. During the dropwise addition of 70 to 90 mL and preferably 80 mL of 2N sodium hydroxide under vigorous stirring a small increase in temperature of the reaction mixture is observed. After the end of the sodium hydroxide addition the reaction medium is stirred for 1 to 3 hours and preferably for 1.5 hours. After removal by filtration on celite ® of the residual alloy, the solution is evaporated. The obtained residue is redissolved in 100 mL of water and the resulting solution extracted with chloroform. After drying over magnesium sulfate and evaporating the organic phase, 1.2 g of a light oily material is isolated and identified as the tetraamine corresponding to the general formula (VI). The yield is of 45%.

$^1$H NMR (D$_2$O) :δ: 1.84 (q, 2H, CH$_2$—CH$_2$—CH$_2$); 1.99 (q, 2H, CH$_2$—CH$_2$—CH$_2$); 2.81 (t, 2H, CH$_2$); 2.83 (t, 2H, CH$_2$); 2.98 (t, 2H, CH$_2$) ; 3.12 (t, 2H, CH$_2$); 3.38 (t, 2H, CH$_2$); 3.40 (t, 2H, CH$_2$); 4.52 (s, 2H, CH$_2$—Py); 7.96 (dd, 1H, H$_5$—Py); 8.59 (d, 1H, H$_4$—Py); 8.67 (d, 1H, H$_2$13 Py).

-Step 3.

Synthesis of 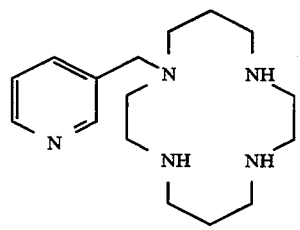

To a solution of 2.37 g of nickel chloride hexahydrate in 20 to 40 mL and preferably 28.5 mL of water, 2.65 g of the N-substituted tetraamine isolated in the previous step are added. After stirring at room temperature for a few minutes, 1.7 ml of a 40% aqueous solution of glyoxal are added. The reaction medium is then stirred overnight. To this solution are then added 1.19 to 3.28 g and preferably 2.24 g of Raney alloy followed by a fast dropwise addition of 20 to 60 mL and preferably 45 mL of 2N sodium hydroxide. After stirring the reaction medium at room temperature for 1 to 2 hours and preferably for 1.5 hours the residual alloy is filtered off on celite ®, then the solution is acidified to pH=3 by addition of concentrated perchloric acid, HClO$_4$. The solution is then extracted with nitromethane and the organic phase is dried over magnesium sulfate. After filtration the solvent is evaporated under reduced pressure. The perchlorate salt of N-(3-picolyl)-1,4,8,11-tetraazacyclo- tetradecane is isolated as a solid with a yield of 70%.

The overall yield of the synthesis starting from acrylonitrile is of 19%.

$^1$H NMR (D$_2$O): δ: 2.06 (quint, 2H, CH$_2$—CH$_2$—CH$_2$); 2.24 (quint, 2H, CH$_2$—CH$_2$—CH$_2$); 2.7 (t, 2H) ; 2.91 (t, 2H) ; 2.24–3.72 (m, 12H) ; 4.03 (s, 2H, CH$_2$—Py) ; 8.09 (t, 1H, H$_5$—Py) ; 8.55 (d, 1H, H$_4$—Py) ; 8.60 (d, 1H, H$_6$—Py); 8.83 (s, 1H, H$_2$—Py).

EXAMPLE IV: Synthesis of N-(2-picolyl)-1,4,8,11-tetraazacyclotetradecane

-Step 1.

Synthesis of 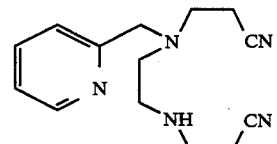

By strictly following the experimental procedure described in Step 1 of Example III the dinitrile is isolated as an oily material and used in the next step without further purification.

$^1$H NMR (D$_2$O):δ: 2.70 (t, 2H, CH$_2$); 2.89 (t, 2H, CH$_2$); 2.90 (t, 4H, CH$_2$) (starting dinitrile); 3.02 (t, 2H, CH$_2$); 3.06 (t, 2H, CH$_2$) ; 3.30 (t, 2H, CH$_2$); 3.34 (t, 2H, CH$_2$); 3.37 (t, 4H, CH$_2$) (starting dinitrile); 3.42 (s, 4H, CH$_2$) (starting dinitrile); 4.12 (s, 2H, —CH$_2$—Py); 8.01 (dd, 1H, H$_4$—Py); 8.06 (dd, 1H, H$_3$—Py) ; 8.56 (td, 1H, H$_5$—Py); 8.76 (dd, 1H, H$_6$—Py).

-Step 2.

Synthesis of 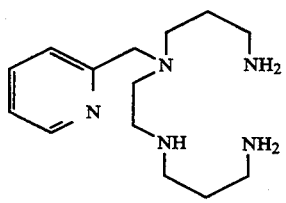

By strictly following the experimental procedure described in Step 2 of Example III the above N-substituted linear tetraamine is isolated as a light oily material with a yield of 45%.

$^1$H NMR (D$_2$O) :δ: 1.85 (q, 2H, CH$_2$—CH$_2$—CH$_2$); 2.00 (q, 2H, CH$_2$—CH$_2$—CH$_2$) ; 2.81 (t, 2H, CH$_2$) ; 2.84 (t, 2H, CH$_2$) ; 2.99 (t, 2H, CH$_2$); 3.11 (t, 2H, CH$_2$); 3.38 (t, 2H, CH$_2$); 3.41 (t, 2H, CH$_2$) ; 4.48 (s, 2H, CH$_2$—Py); 8.00 (dd, 1H, H$_4$—Py); 8.07 (dd, 1H, H$_3$—Py); 8.60 (td, 1H, H$_5$—Py); 8.78 (dd, 1H, H$_6$—Py).

-Step 3.

Synthesis of 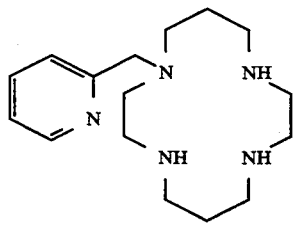

By strictly following the experimental procedure described in Step 3 of Example III the expected N-(2-picolyl)-1,4,8,11 tetraazacyclotetradecane perchlorate salt is isolated as a white solid with a yield of 70%.

The overall yield of the synthesis of this ligand starting from acrylonitrile is of 19%.

$^1$H NMR (D$_2$O):δ: 2.04 (quint, 2H); 2.14 (quint, 2H); 2.76 (t, 2H); 2.92 (t, 2H); 3.17-3.43 (m, 10H); 3.48 (t, 2H); 4.10 (s, 2H, CH$_2$—Py); 7.92 (m, 2H); 8.54 (t, 1H); 8.87 (d, 1H).

EXAMPLE V: Synthesis of 1,4-dibentyl-1,8,11-tetraazacyclotetradecane nickel perchlorate.

-Step 1.

Synthesis of 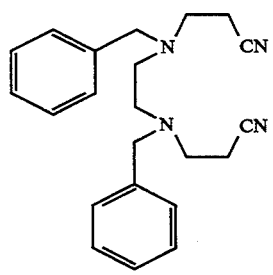

In 550 mL of absolute ethanol cooled down to 5° C., 70 g of the dinitrile obtained in Step 1 of the synthesis of cyclam (Example I) are added, followed by the dropwise addition of 50mL of benzyl chloride. The reaction mixture is heated for 1 to 2 hours and preferably for 1.5 hours and then allowed to cool down to room temperature. The starting unreacted amine protonated by HBr and is filtered off as a white solid before evaporating the ethanol. The orange oily material thus obtained is redissolved in 200 to 240 mL and preferably 220 mL of water and added of 80 to 120 mL and preferably 100 mL of chloroform. The pH is then raised to 8 by addition of sodium hydroxide and the two phases are vigorously stirred for 20 minutes. After separation of the organic phase and drying over magnesium sulfate a yellow-orange oily material is obtained. The dibenzyl derivative is isolated with a yield of 30% by column chromatography on silica under pressure, eluting with a 5/1 mixture of methylene chloride/heptane.

$^1$H NMR (D$_2$O) : δ: 2.87 (t, 4H, CH$_2$—CH$_2$—CN); 3.36 (s, 4H, NH—CH$_2$—CH$_2$—NH); 3.41 (t, 4H, NH,—CH$_2$—CH$_2$); 4.25 (s, 4H, CH$_2$—Ph); 7.27 (m, 10H, Ph).

-Step 2.

Synthesis of 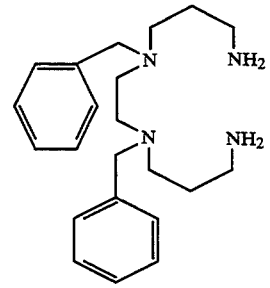

To 3 g of the dibenzyl derivative isolated in Step 1, diluted in 30 to 100 mL and preferably in 64 mL of ethanol, 3 to 9 g and preferably 5.8 g of Raney alloy are added and followed by a fast dropwise addition of 30 to 100 mL and preferably of 64 mL of 2N sodium hydroxide. The reaction mixture is then vigorously stirred for 1 to 2 hours and preferably to 1.5 hours and the residual alloy filtered off on celite ®. The solution is then evaporated to dryness leading to a crude material which is redissolved in water and finally extracted with chloroform. After drying the organic phase over magnesium sulfate and evaporating the solvent, the expected dibenzylated linear tetraamine is isolated with a yield of 76%.

$^1$H NMR (D$_2$O):δ: 1.96 (q, 4H, CH$_2$—CH$_2$—CH$_2$); 2.82 (t, 4H, CH$_2$—CH$_2$—NH$_2$); 3.08 (t, 4H, NH—CH$_2$—CH$_2$); 3.28 (s, 4H, NH—CH$_2$—CH$_2$—NH); 4.17 (s, 4H, CH$_2$—Ph); 7.25 (m, 10H, Ph).

Step 3.

Synthesis of the compound of formula (IX) with A=—(CH$_2$)$_2$— and R$_1$=R$_2$=—CH$_2$C$_6$H$_5$.

After dissolution of 2.15 g of nickel chloride hexahydrate in 20 to 40 mL and preferably in 28.5 mL of water, 3 g of the N,N'-disubstituted tetraamine isolated in the previous step are added. The mixture is then heated at 65°-70° C. during 15 minutes. After filtering off all insoluble materials, the solution is evaporated to dryness. The crude resulting green solid is dissolved in 15 to 25 mL and preferably in 20 mL of chloroform, the insoluble materials are filtered off, the solution is dried over magnesium sulfate, filtrated and evaporated to dryness under reduced pressure. The obtained green solid is then washed with ether and dried under vacuum. The yield of this reaction is of 50%.

To a solution of 1 g of this solid in 10 to 30 mL and preferably in 20 mL of water, 0.23 mL of 40% aqueous glyoxal is added dropwise. The reaction mixture is then stirred overnight. To this solution 1.08 to 2.98 g and preferably 2.03 g of Raney alloy are added, followed by a fast dropwise addition of 20 to 60 mL and preferably of 40 mL of 2N sodium hydroxide. After stirring at room temperature for 1 to 2 hours and preferably for 1.5 hour the residual alloy is filtered off on celite ® and the solution is acidified to pH=3 by addition of concentrated perchloric acid, $HClO_4$. The 1,4-dibenzyl-1,4,8,11-tetraazacyclotetradecane nickel complex is isolated as the perchlorate salt with a yield of 75%. This complex has physicochemical characacteristics similar to that reported by BAREFIELD et al in Inorganic Chemistry, 1976, 15(6), 1370 for a compound of the same formula.

The free dibenzylated ligand may be obtained by a demetalation reaction of the above complex using cyanide ions in a similar way as described in Example I.

What is claimed is:

1. A compound of formula (X):

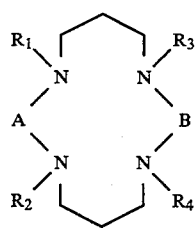
(X)

in which A and B, identical or different, represent:
a chain —$CH_2$—$CH_2$— or —$CH_2$—CHT—$CH_2$—, in which T represents a hydrogen or a group P or $P_1$, where $P_1$ is an alkyl group of 1 to 5 carbon atoms, substituted or not by one or several groups P, where P represents:

an aromatic cycle of 6 to 14 carbon atoms eventually substituted in at least one of its ortho, meta or para positions by a halogen atom, an alkyl group of 1 to 4 carbon atoms, an alkoxy group of 1 to 4 carbon atoms, a hydroxy, an aryl group from 6 to 14 carbon atoms, an aromatic heterocycle as described below, a nitro group, a —$(CH_2)_u$—COR group in which R has the same meaning as below and u is an integer number ranging from 0 to 4, or a primary amine or an amine substituted by one or two alkyl groups of 1 to 4 carbon atoms, an aromatic heterocycle having at least 5 atoms with 3 to 12 carbon atoms and having 1 or 2 hetero atoms selected from the group consisting of nitrogen and sulfur, and eventually substituted in at least one of its ortho, meta or para positions by a halogen atom, an alkyl group of 1 to 4 carbon atoms, an alkoxy group of 1 to 4 carbon atoms, a hydroxy, an aromatic heterocycle as described above, an aryl group from 6–14 carbon atoms, a nitro group, a —$(CH_2)_u$—COR in which R has the same meaning as below and u represents an integer number ranging from 0 to 4, or a primary amine or an amine substituted by one or two alkyl groups of 1 to 4 carbon atoms, a primary amine of an amine substituted by one or two alkyl groups of 1 to 4 carbon atoms, a —CN group, an alkyl group of 1 to 4 carbon atoms, an alkoxy group of 1 to 4 carbon atoms, a hydroxy group, a nitro group, a halogen atom, a group

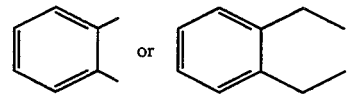

$R_1$ and $R_4$ represent a hydrogen, $R_2$ and $R_3$, identical or different, represent:
a group P or $P_1$, wherein P and $P_1$ have the above described meanings, the —COR group excepted, in which R represents: a hydroxyl (—OH), a primary amine, an amine substituted by one or two alkyl groups of 1 to 4 carbon atoms, a —OR' function in which $R_1$ represents either an alkyl group of 1 to 4 carbon atoms, an aromatic cycle of 6 to 14 carbon atoms;

a group

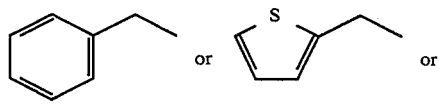

with the proviso that the compound not have A and B identical as —$CH_2$—$CH_2$— or —$CH_2$—$CH_2$—$CH_2$— and one or both of $R_1$ and $R_2$ are hydrogen.

2. A compound of claim 1 wherein T is —$(CH_2)_q$—$NH_2$ where q is an integer from 1 to 5.

3. A compound of claim 2 wherein T is —$(CH_2)_q$—$NH_2$ where q is an integer from 1 to 5.

4. A compound of formula (II):

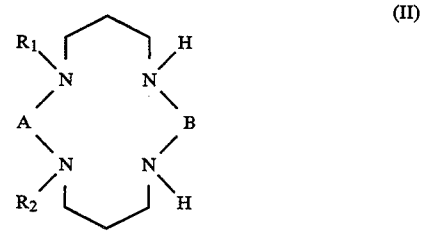
(II)

in which A and B are identical or different and are a chain —$CH_2$—$CH_2$— or $CH_2$—CHT—$CH_2$— in which T represents a hydrogen atom or a group P or $P_1$, where $P_1$ an alkyl group of 1 to 5 carbon atoms, substituted or not by one or several groups P, where P represents:

an aromtic cycle of 6 to 14 carbon atoms eventually substituted in at least one or its ortho, meta or para positions by a halogen atom, an alkyl group of 1 to 4 carbon atoms, an alkoxy group of 1 to 4 carbon atoms, hydroxy, an aryl group from 6 to 14 carbon atoms an aromatic heterocycle as described below, a nitro group, a —$(CH_2)_u$—COR group in which R represents hydroxyl, primary amine or mine substituted by one or two alkyl groups of 1 to 4 carbon atoms, or —OR' in which R' represents either an alkyl group of 1 to 4 carbon atoms or an aromatic cycle of 6 to 14 carbon atoms, an aromatic heterocycle at least five atoms and having 1 or 2 hetero atoms selected from the group consisting of nitrogen, and sulfur, and from 3 to 12 carbon atoms, eventually substituted in at least one of its ortho, meta or para positions by a halogen atom, an alkyl group of 1 to 4 carbon atoms, an alkoxy group of 1 to 4 carbon atoms, hydroxy, an aromatic heterocycle as described above, an aryl group from 6 to 14 carbon atoms, a nitro group, a —(CH$_2$)$_u$—COR in which R has the same meaning as above and u represents an integer number ranging from 0 to 4, or a primary amine or an amine substituted by one or two alkyl groups of 1 to 4 carbon atoms, a primary amine or an amine substituted by one or two alkyl groups of 1 to 4 carbon atoms, a —CN group, an alkyl group of 1 to 4 carbon atoms, an alkoxy group of 1 to 4 carbon atoms, a hydroxy group, a nitro group, a halogen atom, or a group

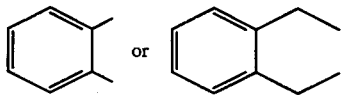

$R_1$ and $R_2$, identical or different, represent a hydrogen, a group P or $P_1$, where P and $P_1$ have the same meanings as above, a group

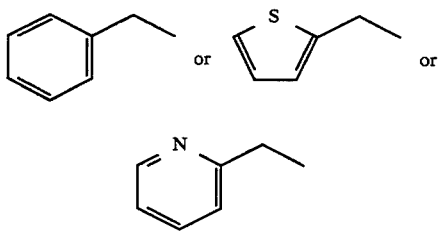

with the proviso that the compound not have A and B identical as CH$_2$—CH$_2$— or —CH$_2$—CH$_2$—CH$_2$— and one or both of $R_1$ and $R_2$ are hydrogen.

5. A compound of claim 1 wherein T is a group P or $P_1$, and P is not an alkyl group of 1 to 4 carbon atoms or an alkoxy group of 1 to 4 carbon atoms.

6. A compound of claim 4 wherein T is a group P or $P_1$, and P is not an alkyl group of 1 to 4 carbon atoms or an alkoxy group of 1 to 4 carbon atoms.

7. A compound of claim 1 wherein T is a group P or $P_1$, and P is not an alkyl group of 1 to 4 carbon atoms, an alkoxy group of 1 to 4 carbon atoms or an aromatic cycle substituted with an alkyl group of 1 to 4 carbon atoms, an alkoxy group of 1 to 4 carbon atoms, a hydroxy or an aryl group.

8. A compound of claim 4 wherein T is a group P or $P_1$, and P is not an alkyl group of 1 to 4 carbon atoms, an alkoxy group of 1 to 4 carbon atoms or an aromatic cycle substituted with an alkyl group of 1 to 4 carbon atoms, an alkoxy group of 1 to 4 carbon atoms, a hydroxy or an aryl group.

* * * * *